United States Patent [19]

Segar

[11] Patent Number: 5,593,419
[45] Date of Patent: Jan. 14, 1997

[54] FIXED WIRE DILATATION CATHETER WITH DISTAL TWISTABLE SEGMENT

[75] Inventor: Lori K. Segar, Rochester, Minn.

[73] Assignee: C.R. Bard, Inc., Murray Hill, N.J.

[21] Appl. No.: 189,293

[22] Filed: Jan. 31, 1994

Related U.S. Application Data

[63] Continuation of Ser. No. 539,707, Jun. 18, 1990, abandoned.

[51] Int. Cl.⁶ ............................................. A61M 25/10
[52] U.S. Cl. ............................................ 606/194; 604/96
[58] Field of Search .................................. 606/194, 192, 606/193, 196, 96, 103

[56] References Cited

U.S. PATENT DOCUMENTS

| 4,483,340 | 11/1984 | Fogarty et al. |
| 4,552,127 | 11/1985 | Schiff ........................ 606/192 X |
| 4,917,088 | 4/1990 | Crittenden ........................ 606/194 |
| 5,417,658 | 5/1995 | Loney et al. |

FOREIGN PATENT DOCUMENTS

| 366904 | 10/1990 | Austria . |
| 363203 | 4/1990 | European Pat. Off. . |
| WO89/11306 | 11/1989 | WIPO . |

*Primary Examiner*—Michael H. Thaler
*Attorney, Agent, or Firm*—Bookstein & Kudirka, P.C.

[57] ABSTRACT

A fixed-wire type of balloon dilatation catheter has a small diameter and can be steered to and passed to and through narrow stenoses. The catheter has a balloon at its distal end which is collapsible to a low profile to enable it to be passed through the stenosis. The catheter includes a connection between the distal end of the balloon and the supporting core wire which displays the least resistance to twisting about the core wire when the core wire is rotated with respect to the balloon and the balloon is subsequently inflated. Consequently, any twisting of the catheter about the wire will occur distally of the balloon so as not to obstruct fluid flow through the balloon.

11 Claims, 3 Drawing Sheets

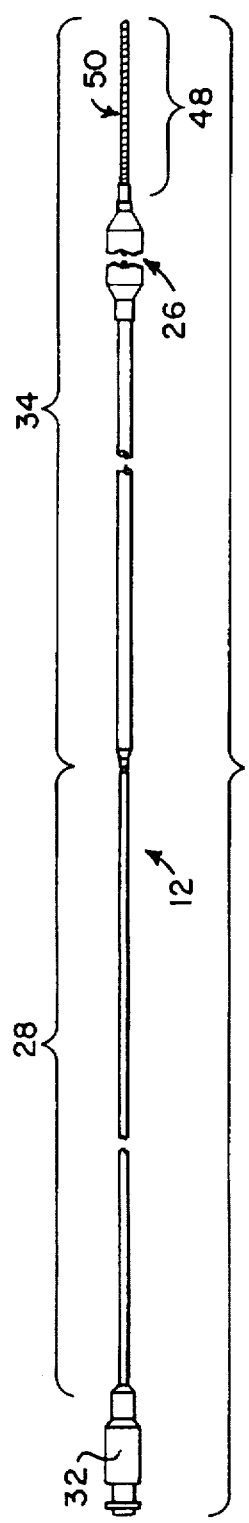
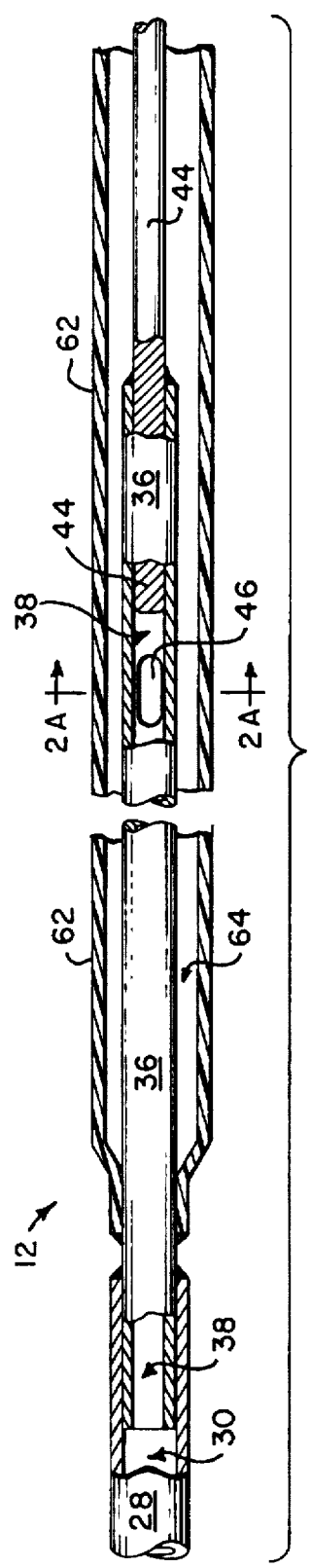
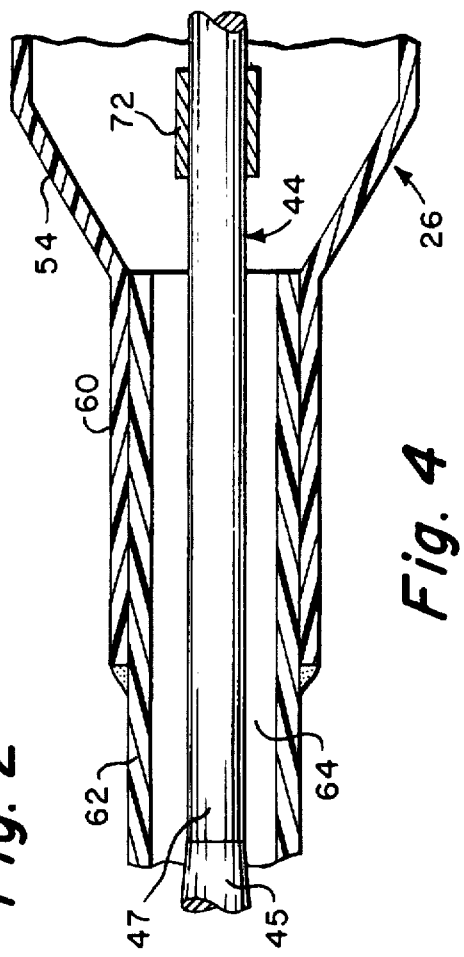
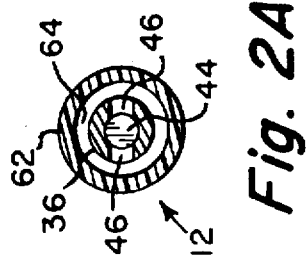

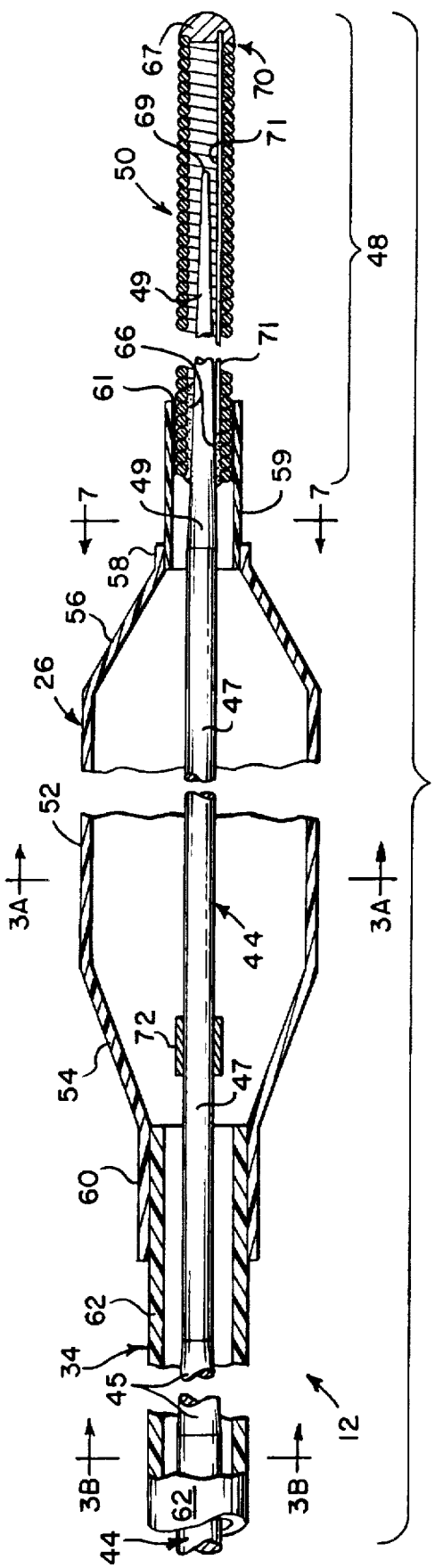
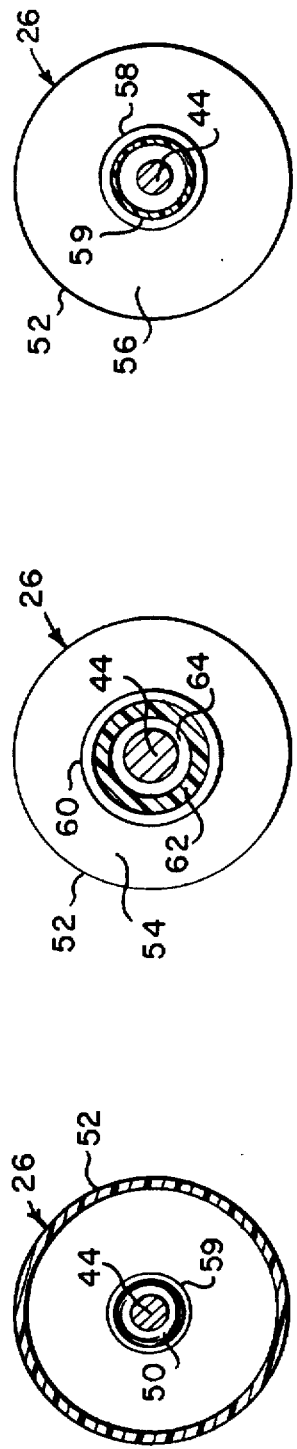
Fig. 3
Fig. 3A
Fig. 3B
Fig. 7

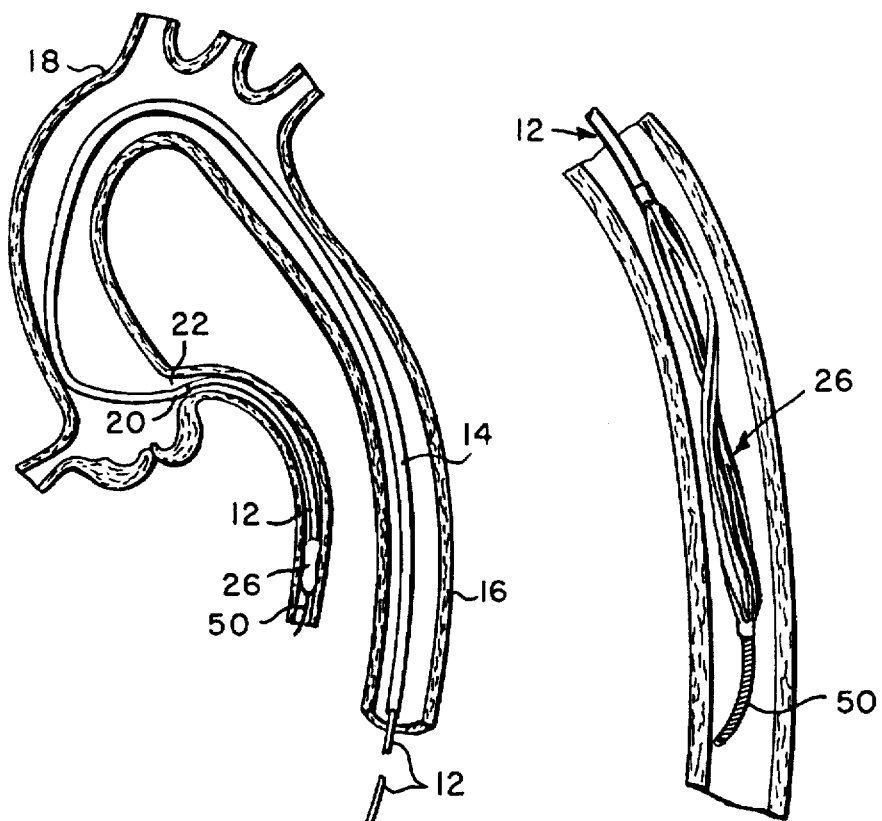
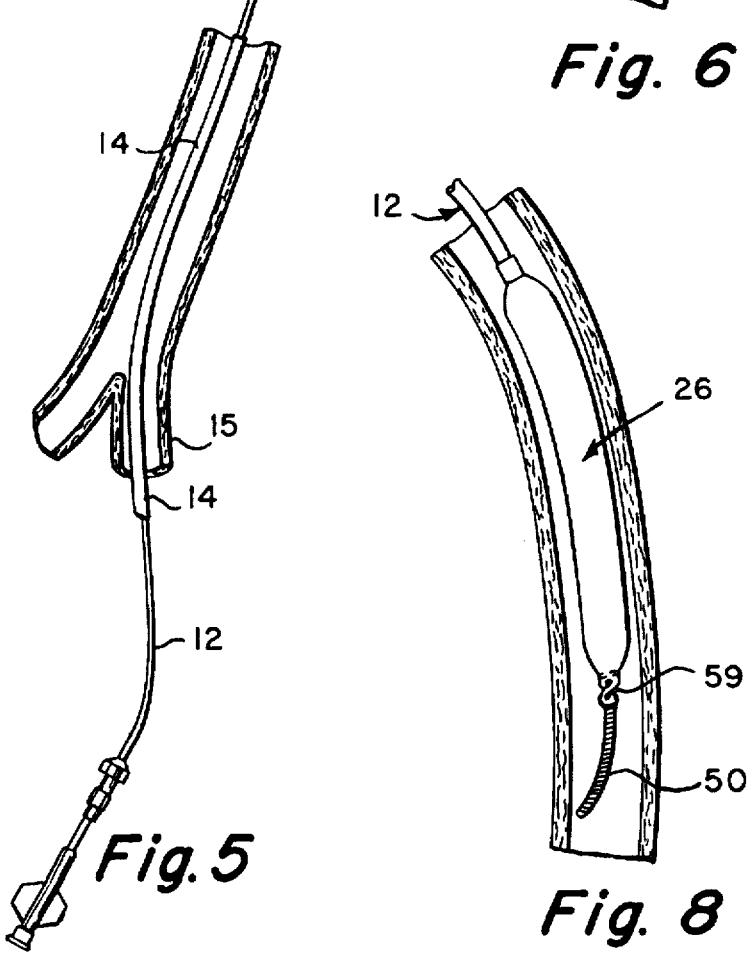
Fig. 6
Fig. 5
Fig. 8

FIXED WIRE DILATATION CATHETER WITH DISTAL TWISTABLE SEGMENT

This application is a continuation of application Ser. No. 07/539,707, filed Jun. 18, 1990 now abandoned.

FIELD OF THE INVENTION

This invention relates to improvements in fixed wire balloon dilatation catheters used to perform angioplasty procedures on stenosed blood vessels.

BACKGROUND OF THE INVENTION

Balloon angioplasty procedures have been used in recent years with increasing success in the treatment of obstructed arteries, such as the coronary arteries. The procedure involves advancing a catheter, having a special balloon at its distal end, to the location of the stenosis. The balloon portion of the catheter is inserted, in its deflated condition, into the stenosis and then is inflated with a liquid under high pressure to compress radially and outwardly the biological material, such as plaque, which forms the stenosis. One type of such dilatation catheter is referred to as a "fixed wire" catheter. Fixed wire catheters are characterized in that the balloon portion at the distal end of the catheter is supported on a central wire that extends through the balloon and to which at least the distal end of the balloon is attached. By way of example, U.S. Pat. Nos. 4,917,088 and 4,582,181 disclose two types of fixed wire catheters. In general, the fixed wire catheters exhibit a low profile, that is, the balloon portion can be deflated and wrapped closely about the supporting wire and, in that configuration, the catheter can be advanced to and into very narrow stenoses and into very small blood vessels. Typically, such fixed wire catheters are steerable in that they can be manipulated from their proximal end to rotate and advance the catheter. By providing the distal end of the wire, which protrudes distally of the balloon, with a slight bend, and by a combination of rotating and advancing movements, the fixed wire catheters can be advanced and steered through a patient's blood vessels to the intended location to be treated.

Although such fixed wire catheters have achieved wide spread use among physicians practising angioplasty, occasionally, they may present some difficulties. In particular, among the difficulties encountered with such fixed wire catheters is that when the core wire is rotated, that sometimes causes the balloon to twist, in an hourglass configuration, about the core wire. Such twisting can obstruct flow of inflation liquid to or from the balloon. Although flow of inflation liquid to the balloon impairs the ability of the balloon to be inflated in order to perform the angioplasty, a more serious condition is presented when the twist in the balloon prevents the balloon from being deflated. It is essentially to be able to deflate the balloon so as to periodically permit some blood flow in the artery and also to be able to withdraw the catheter after the angioplasty procedure has been completed. The consequences of inability to deflate the balloon can be very serious.

It is among the primary objects of the present invention to provide a fixed wire catheter construction in which the risk of the balloon becoming twisted in a manner that adversely effects inflation or deflation of the balloon is avoided.

SUMMARY OF THE INVENTION

The invention involves the provision of a relatively weak, easily twistable segment between the distal end of the balloon and the guidewire. The tubular twistable segment is constructed and dimensioned such that when the guidewire is rotated, any tendency for the balloon to twist about the wire will be taken up by the distal segment which is the most easily twisted portion of the catheter.

It is among the objects of the invention to provide a fixed wire balloon dilatation catheter in which the risk of the balloon becoming twisted in response to rotation of the guidewire is reduced substantially.

Another object of the invention is to provide an improved construction for a fixed wire balloon dilatation catheter in which a portion of the catheter distally of the balloon is the portion of the catheter that is most susceptible to twisting in response to rotation of the guidewire.

Another object of the invention is to provide a fixed wire balloon dilatation catheter in which a relatively weak, twistable tubular segment extends between the distal end of the balloon and is attached, at its other end, to the guidewire.

Still another object of the invention is to provide a fixed wire balloon dilatation catheter having a preferred twistable portion that is of simple construction.

DESCRIPTION OF THE DRAWINGS

The foregoing and other objects and advantages of the invention will be appreciated more fully from the following further description thereof, with reference to the accompanying drawings wherein:

FIG. 1 is a longitudinal, fragmented illustration of the dilatation catheter;

FIG. 2 is an enlarged longitudinal section of the portion of the dilatation catheter which includes the transition region from the proximal segment to the distal segment;

FIG. 2A is a sectional illustration of the transition tube as seen along the line 2A—2A of FIG. 2;

FIG. 3 is an enlarged, diagrammatic, fragmented longitudinal sectional illustration of the balloon portion and distal segment of the dilatation catheter illustrating the manner in which the distal portion of the balloon is joined to the guidewire and including the distal twistable cylindrical segment of the invention;

FIG. 3A is a sectional illustration of the catheter balloon as seen along the lines 3A—3A of FIG. 3;

FIG. 3B is a sectional illustration of the sleeve extension of the catheter when the catheter is in an inflated condition;

FIG. 4 is an enlarged sectional illustration of the juncture of the balloon and the balloon extension sleeve;

FIG. 5 is a diagrammatic, fragmented illustration of a prior art fixed wire balloon dilatation catheter and guide catheter as used in a coronary angioplasty procedure in a configuration in which the balloon may become twisted;

FIG. 6 is an enlarged illustration of the balloon portion of the catheter within a coronary artery in the configuration as suggested in FIG. 5 and illustrating the manner in which the balloon may become twisted;

FIG. 7 is a cross-sectional illustration of the twistable segment as seen along the line 7—7 of FIG. 6; and FIG. 8 is an illustration, similar to FIG. 6, of a fixed wire balloon dilatation catheter incorporating the invention with the guidewire having been rotated sufficiently to cause the distal twistable segment to become twisted about the guidewire.

DESCRIPTION OF THE PREFERRED EMBODIMENT

As shown in FIG. 1 the dilatation catheter 12 is of very slender construction having a cross-section approximately equal to that of a small diameter guide wire.

The dilatation catheter 12 has a balloon 26 which, when collapsed, defines a small cross-sectional configuration so that it can pass through tight stenoses. In its collapsed configuration the catheter balloon 26 as well as the remaining portions of the catheter 12 define an outer diameter close to or corresponding to that of a small diameter guide wire.

The catheter 12, illustrated in FIG. 1, is of the order of about 180 centimeters when used in percutaneous transluminal angioplasty of the coronary arteries (PTCA). The PTCA procedure is illustrated in FIG. 5. The procedure involves initially placing a guide catheter 14 into the patient's arteries, extending from a puncture entry site in the femoral artery 15 in the leg, up through the aorta 16, over the aortic arch 18 with the distal outlet tip 20 of the guide catheter 14 being disposed at the entrance 22 to either the right or left coronary artery (left coronary ostium illustrated). Once the guide catheter 14 is in place, the balloon dilatation catheter then is advanced through the guide catheter and into the coronary arteries. The balloon dilatation catheter may be manipulated and steered by the physician to select branches of the coronary arterial tree so as to advance the catheter to place the balloon portion of the catheter within the stenosis to be treated. As will be described in further detail, manipulation and advancement of fixed wire catheters may tend to cause the balloon to become twisted into somewhat of an hourglass configuration.

The illustrative embodiment of the catheter 12 has a relatively long proximal segment 28 which is formed from narrow, solid wall tubing, such as hypodermic tubing. In the illustrative embodiment, the proximal segment 28 may be of the order of 150 centimeters long. The proximal segment 28 is rigid torsionally so that it can transmit substantially fully and controllably to its distal end rotational motion imparted to the proximal end. As will be described, the distal tip of the catheter can be bent to a preset curve. Rotation applied to the catheter can be controlled to selectively direct and steer the curved distal end of the catheter as it is advanced. The proximal segment 28 also is flexible and can bend longitudinally to follow the curvature of the patient's arterial system. Preferably the proximal segment 28 of the catheter 12 is sufficiently flexible that it can bend to follow the curve of a patient's aortic arch which has a radius of the order of between 2.5 to 3.5 inches in an adult.

As shown more clearly in enlarged FIG. 2, in the fixed wire catheter of the illustrated embodiment of the invention the hollow tubular segment 28 may have an outer diameter of 0.022 inches, a wall thickness of about 0.003 inches and an internal diameter passage 30 of 0.016 inches. A conventional fitting 32 is secured to the proximal end of segment 28 to facilitate connection with an inflation and deflation device, such as a syringe (not shown).

The catheter 12 includes a distal segment 34 which extends from the distal end of the proximal segment 28 to the distal end of the catheter 12. The distal segment 34 includes a narrow diameter elongate support wire 44 which is connected to and extends distally of the proximal segment 28. The support wire 44 is connected to the proximal tubing 28 by a short transition tube 36. The transition tube 36 is about three inches long and also is formed from slender, flexible hypodermic tubing with a smaller diameter than the proximal tube 28. In the illustrative embodiment, the transition tube 36 is formed from hypodermic tubing having an outer diameter of 0.014 inches, a wall thickness of 0.003 inches and an inner diameter of 0.008 inches. The proximal end of the tubing 36 is received within the distal end of the internal passage 30 of the proximal segment 28 and is secured thereto as by soldering or brazing. The solid support wire 44 is attached to the distal end of the transition tube 36. The wire 44, which in the illustrative embodiment is very slender, preferably 0.008 inches diameter, is received in the distal end of the passage 38 of the tubing 36 and is secured by soldering or brazing. The proximal end of the wire 44 that is inserted into the distal end of the tubing 36 may be reduced slightly in diameter to fit within the tubing. The support wire 44 plugs the distal end of the tubing 36. In order to permit the balloon 26 to be inflated and deflated, the transition tube 36 is provided with apertures 46 on opposite sides of the tube wall to provide communication with the internal passages 38, 30 of the catheter. The apertures 46 may be defined by forming a pair of longitudinal slots in the wall of the tubing 36. The support wire 44 provides support for the catheter balloon 26 and also extends distally beyond the balloon 26, to form the core of a leader segment 48. The leader segment includes a helically wound radiopaque coil spring 50 which is attached to the distal end of the core wire 44 in a manner described below.

In an illustrative embodiment of the invention, a distal region of the support wire 44 is of reduced diameter and may be reduced in a step tapered manner. As shown, support wire 44 is about 0.008 inches diameter except for the distal ten to eleven centimeters. As shown in FIG. 3, the distal portion of the support wire 44 includes a first tapered segment 45 that begins ten to eleven centimeters from the distal tip of the wire 44 and tapers from 0.008 inches to about 0.006 inches diameter. A constant diameter cylindrical segment 47 about 3 cm long extends distally from the tapered segment 45. The remaining distal 5 cm of the support wire 44 are tapered, as indicated at 49, from a diameter of 0.006 inches to about 0.002 inches. The proximal end of the balloon, depending on its length, will be disposed generally along the region of the cylindrical segment 47. The proximal end of the spring 50 is attached to the distal tapering segment 49 at a location about 15 to 18 mm from the distal tip of the segment 49.

The catheter balloon 26 may be formed by molding high strength polymeric material in a manner which provides a thin balloon wall not greater than about 0.001 inches thickness and, preferably, having a thickness of the order of 0.0005 inches. The balloon may be manufactured as described in U.S. Pat. No. 4,490,421 issued Dec. 25, 1984 and application Ser. No. 001,759 filed Jan. 9, 1987. That patent and application are hereby incorporated herein by reference, in their entireties; and reference is made thereto for further details concerning the manufacture of the balloon.

As shown in enlarged detail in FIG. 3, the balloon includes a main cylindrical portion 52. By way of example, the catheter balloon 26 may have an outer diameter of from about 1.5 mm to 3.5 mm diameter. As mentioned above, the balloon preferably is formed from a high strength material which will not tend to stretch when inflated. The length of the balloon 26 may be of the order of 15 to 20 mm.

The balloon is formed to include tapering portions 54, 56 at the proximal and distal ends respectively. The distal tapering portion 56 merges into a narrowed neck 58. In accordance with the invention, the narrowed neck 58 in turn is attached to a distal tubular twist member 59. The tubular twist member 59 is attached at its proximal end to the distal neck 58 of the balloon and at its distal end to the support wire in the region of the proximal end of the coil spring 50 at a distal balloon cyanoacrylate adhesive bond 61. As will be described in further detail below, the distal twist member will display the least resistance to becoming twisted in response to rotation of the shaft and support wire so that if twisting does occur, it will occur distally of the balloon 26 so as not to interfere with inflation or deflation of the balloon. By way of example, in the preferred embodiment the distal twist tubular member 59 may be formed from a tube of polyethylene terephthalate having a wall thickness thinner than the balloon necks and comparable to the wall thickness of the central portion of the balloon, namely, of the order of 0.0002 inches–0.0005 inches thickness. The twist member 59 may be of the order of three to ten millimeters in length. The overlap of the distal balloon neck and the twist member 59 may be about one millimeter as in the width of the adhesive bond of the twist member to the spring 50. It has an internal diameter just slightly greater than the outer diameter of the coil spring 50 to which it is bonded. The clearance between the inner diameter of the twist member 59 and outer diameter of the coil spring should be just sufficient to receive an adhesive to make the bond. The adhesive preferably is a cyanoacrylate adhesive. By way of further example, depending on the diameter and size of the catheter, the spring 50 may be of the order of 0.014–0.016 inches outer diameter. Thus, the internal diameter of the twist member 59 may be of the order of 0.0155–0.0175 inches.

The proximal end of the coil spring is soldered securely to the core wire at the region where the distal neck 58 of the Catheter balloon 26 is joined, that is, at the bond 61. The proximal tapering portion 54 merges into a narrowed proximal neck 60.

In order to communicate the interior of the catheter balloon 26 with the inflation/deflation passages 30, 38 of the tubing, an extension sleeve 62 is adhesively attached to the proximal neck 60. The extension sleeve 62 extends proximally over the support wire 44. The proximal end of the extension sleeve 62 may be formed from polyethylene and is securely and adhesively attached to the outer surface of the transition tube 36, where it joins the main tube 28. The extension sleeve 62 defines an annular passage 64 about the support wire 44. The annular passage 64 provides communication between the apertures 46 and the interior of the balloon 26 for inflation and deflation of the balloon. In the preferred construction for the catheter, the distal end of the extension sleeve extends fully through the proximal neck 60 of the balloon to the juncture of the neck 60 and tapered conical portion 54. The overlapping areas of the neck extension 62 and proximal neck 60 are bonded by an appropriate adhesive, such as cyanoacrylate. It is desirable to avoid joining the proximal neck 60 in a manner that would permit any portion of the proximal neck 60 to span freely between the end of the proximal sleeve 62 and the cone 54. In such a non-coextensive portion, it might define a weakened region which could tend to twist to a closed configuration about the core wire. In accordance with the invention, it is desired that any such twisting, if it occurs at all, should occur distally of the balloon.

As shown in FIG. 3 the leader segment 48 which extends distally of the balloon 26 is of increasing flexibility in a distal direction to provide a relatively soft, flexible leading tip which reduces the chance of trauma or injury to the blood vessel. In the illustrative embodiment the leader segment is about 3 centimeters long. The coil spring 50 is soldered, at its proximal end to the support wire 44, as indicated at 66. The distal tip 69 of the support wire 44 terminate, short of the distal tip of the coil spring 50. The distal tip 70 of the coil spring 50 may extend about five mm beyond the distal tip 69 of the support wire 44 and defines a highly flexible bumper tip. A rounded weld bead 67 is formed at the distal tip of the spring 50. The leader segment 48 is of increasing flexibility in a distal direction. The support wire 44 is taper ground and, for example, may be ground smoothly to a 0.002 inch diameter at its distal tip 69.

The distal tip 70 of the coil spring 50 includes a flexible and bendable stainless steel shaping ribbon 71 which is secured to the distal tip 69 of the support wire at one end, and to the distal weld bead 67 at its other end. The shaping ribbon is of slender, rectangular cross section, of the order of 0.001 inches by 0.002 inches. The shaping ribbon is adapted to be bent to a desired curve and to retain that curve when relaxed. The preset curve enables the catheter 12 to be steered by rotation of the catheter from its proximal end. The catheter can be rotated to direct the prebent distal tip 70 in selective directions as desired within the patient's blood vessels.

The catheter also is provided with a radiopaque marker band 72 which preferably is formed from platinum. The marker band 72 is located proximally of the main cylindrical portion of the balloon 26. In the illustrative embodiment it is securely attached to the support wire 44. The marker band 72 provides a means by which the physician can verify, fluoroscopically, the position of the catheter balloon 26.

In order that the catheter may be passed through the lumen of a catheter which may guide the catheter to the coronary arteries, the catheter balloon 26 also must be collapsible to a shape and size which can be passed through the lumen of that guiding catheter. The catheter accomplishes these objectives by using the slender, small diameter support wire 44 extending through the balloon and by using a balloon with a very thin but high strength wall, the operation and function of this aspect of the illustrative catheter is described in detail in U.S. Pat. No. 4,917,088 which is incorporated herein and to which reference is made. The balloon may be formed from a high strength thin material having a wall thickness preferably not more than about 0.001" and may be of the order of 0.0002"–0.0005" thick. The catheter balloon is collapsible to a diameter which is about one fourth of its inflated diameter and which can pass easily through the main lumen of the guiding catheter.

In use, a larger diameter guiding catheter 14 through which the dilatation catheter 12 can be passed is inserted initially in the patient's arterial system, usually through the femoral artery 15 and is advanced through the aortic arch 18 to locate the distal tip of the guide catheter at the coronary ostium leading to the coronary artery to be treated. After the larger guiding catheter 14 has been positioned, the slender balloon catheter 12 is advanced through the guide catheter with its balloon 26 in a collapsed configuration. The dilatation catheter 12 thus can be advanced out of the distal opening of the guiding catheter and, with its balloon 26, in a collapsed configuration, can be advanced through and manipulated in the patient's coronary arteries toward the arterial segment where the stenosis to be treated is located. Once the catheter has been manipulated to the stenosis it is inserted into and through the stenosis. The dilatation catheter balloon 26 then may be inflated under pressure to expand forcefully the catheter balloon 26 to its maximum diameter thereby enlarging the passageway through the stenosis. When the catheter balloon 26 has been inflated to enlarge the opening through the stenosis the catheter balloon 26 is collapsed by aspirating the catheter. The catheter then may be withdrawn from the patient.

As described above, the catheter has a very flexible distal segment 34. The proximal segment 28, as described, is sufficiently flexible so that it can bend relatively easily through the aortic arch. The bends from the descending aorta, into the coronary ostium and thereafter through the coronary arteries are sharper and shorter radiused. The length of the more flexible distal segment 34 is sufficient so that the catheter balloon can reach deeply into the arterial tree without requiring the stiffer proximal tubing 28 to pass through relatively sharp bends, such as the bend from the guide catheter to the coronary ostium. The distal segment 34, which consists substantially of the thin, flexible support wire 44 is able to make the relatively sharp bends with ease. Thus, the only portion of the catheter 12 which actually enters the coronary artery is that which includes the slender support wire 44. This support wire is very flexible and is more easily bent to be able to negotiate shorter radius bends encountered in the coronary arterial tree.

The catheter is highly steerable due in large measure to the solid wall of the tubing in the elongate proximal segment 28 of the catheter. The tubing is substantially torsionally rigid and tends to transmit controllably substantially all of its rotation applied at the proximal end to the distal end. Although the intermediate segment of the catheter, which includes the slender 0.008 inch diameter wire is too small a diameter to effectively transmit torque over relatively long distances, the distal segment 34 is relatively short, preferably about twenty-five centimeters and, therefore, does not have too great of an adverse effect on the torque transmission from the proximal end of the catheter to the distal end. The distal segment preferably is no longer than about 25 centimeters, as compared to the solid wall tubular proximal segment which is approximately 150 centimeters long. Thus, by forming a bend in the distal tip 70 of the leading segment, the direction of the catheter 12 can be controlled by rotating the catheter from the proximal end.

FIGS. 5 and 6 illustrate the manner in which a fixed wire prior art angioplasty catheter may tend to become twisted in its balloon region. When the balloon catheter is in position though the guide catheter, a significant portion of the balloon catheter proximally of the balloon may pass through a number of curves, some of which may be quite tortuous. The curves will include at least the coronary arch 18 and at least two more curves defined at the distal end of the catheter. Additionally, the catheter may be expected to pass through one or more additional sharply radiused curves within the coronary arteries themselves, some of which may be highly tortuous. The passage of the balloon dilatation catheter through a number of such curves tends to restrict the ability of portions of the catheter, particularly the segment proximally of the balloon from rotating. In the presently described embodiment, such resistance to rotation may be expected to develop in the region of the neck extension sleeve 62. Consequently, it may occur that when the shaft and support wire 44 of the catheter are rotated, to rotate the leader segment 48, the distal end of the extension sleeve 62 may have little or no rotation while the rotation of the wire is transmitted to the distal end of the balloon. Because the proximal end of the balloon is constrained from rotating, resulting from its attachment to the distal end of the extension 62, there is a relative twisting motion applied to the proximal and distal ends of the balloon. Consequently, the balloon may become twisted to the hourglass configuration as suggested in FIG. 6.

In accordance with the present invention, the provision of the torsionally weak, distal tubular extension 59 provides a torsionally weak segment between the support wire and the distal end of the balloon at a location distally of the balloon. With the present invention, should the proximal end of the balloon be constrained from rotating, rotation of the core wire will be transmitted to the twist member 59. Where twist member 59 forms the torsionally weakest portion of the device, it will become twisted rather than the balloon. As a result, the balloon will not become twisted and flow of inflation liquid to and from the balloon will not be impaired.

From the foregoing, it will be appreciated that the invention provides a balloon dilatation catheter of the fixed wire type in which any tendency for a portion of the catheter to become twisted about the core wire in response to rotation of the core wire is caused to occur at a location distal of the dilatation balloon. The invention thus avoids potential difficulties that otherwise might arise in the event that a catheter became twisted about the wire in the region of the balloon.

It should be understood, however, that the foregoing description of the invention is intended merely to be illustrative thereof and that other modifications and embodiments of the invention will be apparent to those skilled in the art without departing from its spirit.

Having thus described the invention what I desire to claim and secure by Letters Patents is:

1. In a balloon dilatation catheter having proximal and distal ends and an integral support wire and a balloon at the distal end of the catheter, the distal end of the catheter having a construction comprising:

the balloon having a central cylindrical portion and proximally and distally extending tapering portions, each of the tapering portions terminating in a reduced diameter cylindrical neck portion;

the support wire extending through the balloon;

a separate tubular distal extension member connected integrally to and extending distally from the distal neck of the balloon, the distal end of the distal extension being attached to the support wire;

the distal extension being constructed and supported to present less resistance to twisting than the balloon and the more proximal portions of the catheter.

2. A balloon dilatation catheter as defined in claim 1 wherein the balloon and distal extension member are formed from the same polymeric material, the distal extension having a wall thickness not greater than the wall thickness of any portion of the balloon.

3. A balloon dilatation catheter as defined in any of claims 1 or 3 wherein the catheter is dimensioned and adapted to be advanced into the coronary artery from a percutaneous insertion site.

4. A balloon dilatation catheter as defined in claim 1 further comprising:

the distal end of the twistable extension member being attached adhesively to the support wire and having a torsionally weak, twistable segment free and unsupported between its points of connection to the support wire and the distal neck of the balloon.

5. A balloon dilatation catheter as defined in claim 1 further comprising:

the wall thickness of the distal neck of the balloon being greater than the wall thickness of the central portion of the balloon, with the wall thickness of the twistable extension member being thinner than that of the distal neck of the balloon.

6. A balloon dilatation catheter as defined in claim 1 wherein the length of the distal twistable extension member is about 3 to 10 millimeters.

7. A balloon dilatation catheter as defined in claim 1 further comprising:

the support wire having a distal leader segment that extends substantially beyond the distal end of the balloon and is flexible to reduce the risk of injury to the blood vessel.

8. A balloon dilatation catheter as defined in claim 7 wherein the distal leader segment comprises a coil spring to which the distal end of the twistable extension member is attached.

9. A balloon dilatation catheter as defined in claim 7 wherein the internal diameter of the distal twistable extension member is just slightly greater than the outer diameter of the leader segment to which it is bonded.

10. A balloon dilatation catheter as defined in claim 7 further comprising, a shaping ribbon disposed within the leader segment to facilitate imparting a relaxed bent shape to the leader segment.

11. A balloon dilatation catheter as defined in claim 1 wherein the balloon is blow-molded.

\* \* \* \* \*